(12) United States Patent
Swartz et al.

(10) Patent No.: US 9,222,122 B2
(45) Date of Patent: Dec. 29, 2015

(54) SYSTEM AND METHOD FOR RAPID DETECTION AND IDENTIFICATION OF NUCLEIC ACID LABELED TAGS

(71) Applicant: SRC, Inc., Syracuse, NY (US)

(72) Inventors: Mary F. Swartz, Princeton, NJ (US); William McKay, East Syracuse, NY (US)

(73) Assignee: SRC, Inc., Syracuse, NY (US)

( * ) Notice: Subject to any disclaimer, the term of this patent is extended or adjusted under 35 U.S.C. 154(b) by 284 days.

(21) Appl. No.: 13/682,344

(22) Filed: Nov. 20, 2012

(65) Prior Publication Data

US 2014/0141433 A1 May 22, 2014

(51) Int. Cl.
*C12P 19/34* (2006.01)
*C12Q 1/68* (2006.01)

(52) U.S. Cl.
CPC ........................ *C12Q 1/68* (2013.01)

(58) Field of Classification Search
CPC ................ C12Q 1/68; C12Q 2525/15; C12Q 2563/155; C12Q 2563/159; C12Q 2563/185; C12Q 2565/514
USPC ....................................................... 435/91.2
See application file for complete search history.

(56) References Cited

U.S. PATENT DOCUMENTS

| | | | |
|---|---|---|---|
| 4,683,195 | A | 7/1987 | Mullis et al. |
| 6,623,928 | B2 | 9/2003 | Van Ness et al. |
| 6,858,412 | B2 | 2/2005 | Willis et al. |
| 7,262,030 | B2 | 8/2007 | Chen |
| 7,381,547 | B2 | 6/2008 | Tsang et al. |
| 2003/0003490 | A1 | 1/2003 | Fan et al. |
| 2006/0003350 | A1 | 1/2006 | Tsang et al. |
| 2006/0024711 | A1 | 2/2006 | Lapidus et al. |
| 2007/0059700 | A1 | 3/2007 | Tao et al. |
| 2009/0075261 | A1* | 3/2009 | Hayward et al. ................... 435/6 |
| 2010/0015626 | A1 | 1/2010 | Oliphant et al. |
| 2010/0086918 | A1 | 4/2010 | Carson et al. |
| 2010/0105037 | A1 | 4/2010 | Fu |
| 2010/0227320 | A1 | 9/2010 | Fu |
| 2010/0330619 | A1 | 12/2010 | Willis et al. |
| 2011/0118137 | A1 | 5/2011 | Thompson |
| 2011/0207131 | A1 | 8/2011 | Fu |

FOREIGN PATENT DOCUMENTS

| | | |
|---|---|---|
| WO | 2006073436 A2 | 7/2006 |
| WO | 2007061284 A1 | 5/2007 |

OTHER PUBLICATIONS

Coiras et al., "Simultaneous detection of fourteen respiratory viruses in clinical specimens by two multiplex reverse transcription nested-PCR assays", Journal of Medical Virology Mar. 2004; 72(3): pp. 484-495.

Elden et al., "Simultaneous Detection of Influenza Viruses A and B Using Real-Time Quantitative PCR". Journal of Clinical Microbiology, Jan. 2001; 39(1): pp. 196-200.

* cited by examiner

*Primary Examiner* — Cynthia B Wilder
(74) *Attorney, Agent, or Firm* — George R. McGuire; Bond Schoeneck & King, PLLC

(57) ABSTRACT

A method for detecting and identifying nucleic acid tags. A nucleic acid tag comprising a nucleotide-support platform attached to a nucleic acid molecule is created or selected and then immobilized on or in an item, or seeded within an area of interest. Samples are obtained from the surface of an item that has potentially been labeled, and an initial screen is conducted using universal primers to determine which samples contain nucleic acid tag. A multiplex screen is conducted on samples testing positive for nucleic acid tag in order to identify which of a plurality of nucleic acid tags are present on or in the item of interest.

14 Claims, 13 Drawing Sheets

|  | TAGS 1-5 | TAGS 6-10 | TAGS 11-15 | TAGS 16-20 |
|---|---|---|---|---|
| Sample 1 | YES | YES | YES | YES |
| Sample 2 |  | YES | YES |  |
| Sample 3 | YES |  |  |  |
| Sample 4 | YES |  |  | YES |

FIG. 13

|  | Potential Tags in Sample | Tags Confirmed Not in Sample |
|---|---|---|
| Sample 1 | 1-20 |  |
| Sample 2 | 6-15 | 1-5, 16-20 |
| Sample 3 | 1-5 | 6-20 |
| Sample 4 | 1-5, 16-20 | 6-15 |

FIG. 14

SYSTEM AND METHOD FOR RAPID DETECTION AND IDENTIFICATION OF NUCLEIC ACID LABELED TAGS

BACKGROUND OF THE INVENTION

1. Field of the Invention

The present invention relates to systems and methods for using nucleic acid tags, and, more particularly, to systems and methods for rapidly and efficiently detecting and identifying nucleic acid tags.

2. Description of the Related Art

The physical characteristics of a nucleic acid molecule make it uniquely suitable for use as a secure information-storage unit. In addition to being odorless and invisible to the naked eye, a nucleic acid molecule can store vast amounts of information. It has been estimated that a single gram of deoxyribonucleic acid ("DNA") can store as much information as approximately one trillion compact discs ("Computing With DNA" by L. M. Adleman, *Scientific American*, August 1998, pg 34-41).

Nucleic acid molecules are also resilient to decay, even in vitro. Although a nucleic acid molecule typically begins to breakdown when exposed to chemicals, radiation, or enzymes, some nucleic acid molecules can survive for thousands of years. For example, scientists have sequenced the Neanderthal genome using DNA molecules that were recovered from remains dating at least 38,000 years old.

Additionally, nucleic acid molecules are both ubiquitous in nature and largely uncharacterized, with only a fraction of the world's organisms having been sequenced. As a result of this uncharacterized environmental background noise, inadvertent detection of a man-made nucleic acid molecule is unlikely.

To employ the many beneficial characteristics of nucleic acids, these molecules can be incorporated into a secure tag. These tags can be composed of deoxyribonucleotides, ribonucleotides, or similar molecules composed of nucleic acids that are either artificial (such as nucleotide analogues) or are otherwise found in nature. The nucleic acids can range from very short oligonucleotides to complete genomes.

Once a nucleic acid tag is created it can be used for numerous unique security applications including to detect illicit tampering with physical objects. DNA tags have previously been used for other applications. For example, DNA tags have been removably attached to tangible assets to assist in the identification of ownership in the event the asset is lost or stolen. Additionally, it has been proposed that DNA tags be used to prevent counterfeiting by incorporating tags into items during or after production and using detection of such tags to authenticate the items.

Once a nucleic acid tag is deployed for use, it will be necessary to later detect the nucleic acid tag. Similarly, if there are several different nucleic acid tags used, it will be necessary to identify which of the different tags are present. However, there is a continued demand for new and efficient mechanisms for detecting deployed nucleic acid tags, and for methods for identifying which of a plurality of different deployed nucleic acid tags are present, once the existence of a nucleic acid tag is detected.

BRIEF SUMMARY OF THE INVENTION

It is therefore a principal object and advantage of the present invention to provide a nucleic acid tag that can be used in numerous security-related applications.

It is another object and advantage of the present invention to provide systems and methods for detection of nucleic acid tags.

It is yet another object and advantage of the present invention to provide systems and methods for identification of nucleic acid tags.

Other objects and advantages of the present invention will in part be obvious, and in part appear hereinafter.

Embodiments of the invention comprise systems and methods for identifying which of a plurality of nucleic acid tag varieties are present on an item of interest. According to one embodiment, a method comprises the steps of: (i) creating a plurality of nucleic acid tag varieties, wherein each nucleic acid tag variety comprises a nucleotide-support platform attached to a nucleic acid molecule, the nucleic acid molecule of each nucleic acid tag variety comprising a first and a second universal primer region common to all nucleic acid tag varieties, and a first and a second unique primer region unique to each nucleic acid tag variety; (ii) deploying the plurality of nucleic acid tag varieties; (iii) receiving samples from the item of interest; (iv) performing a first screen of each of the samples with a polymerase chain reaction comprising a primer set complementary to the first and second universal primer regions, wherein the presence of one or more of the plurality of nucleic acid tag varieties is confirmed if the polymerase chain reaction results in an amplification product; and (v) performing, on each of the samples for which the presence of one or more of the plurality of nucleic acid tag varieties was confirmed in the first screen, a second screen comprising a series of multiplex polymerase chain reactions, wherein each multiplex polymerase chain reaction comprises a primer set complementary to the first and second unique primer regions of a subset of two or more of the plurality of nucleic acid tag varieties, and wherein the presence of one or more of the nucleic acid tag varieties within the subset is confirmed if the multiplex polymerase chain reaction results in an amplification product. According to another embodiment, the method further comprises the step of performing, on each subset for which the presence of one or more of the nucleic acid tag varieties was confirmed in the second screen, an individual polymerase chain reaction for each nucleic acid tag variety within that subset, wherein each individual polymerase chain reaction comprises a primer set complementary to the first and second unique primer region of one of the plurality of nucleic acid tag varieties, wherein the presence of the nucleic acid tag variety is confirmed if the individual polymerase chain reaction results in an amplification product.

In another implementation, a method for identifying which of a plurality of oligonucleotide tag varieties are present on an item of interest comprises the steps of: (i) creating a plurality of oligonucleotide tag varieties, wherein each oligonucleotide tag variety comprises a nanoparticle nucleotide-support platform attached to a oligonucleotide, the oligonucleotide of each oligonucleotide tag variety comprising a first and a second universal primer region common to all oligonucleotide tag varieties, a first and a second unique primer region unique to each oligonucleotide tag variety, and a nucleic acid spacer unique to each oligonucleotide tag and disposed between said first and second unique primer regions; (ii) deploying the plurality of oligonucleotide tag varieties; (iii) receiving samples from the item of interest; (iv) performing a first screen of each of the samples with a polymerase chain reaction comprising a primer set complementary to the first and second universal primer regions, wherein the presence of one or more of the plurality of oligonucleotide tag varieties is confirmed if the polymerase chain reaction results in an amplification product; (v) performing, on each of the samples for which the presence of one or more of the plurality of oligonucleotide tag varieties was confirmed in the first screen, a second screen comprising a series of multiplex polymerase chain reactions, wherein each multiplex polymerase chain reaction comprises a primer set complementary to the first and second unique primer regions of a subset of two or more of the plurality of oligonucleotide tag varieties, and wherein the presence of one or more of the oligonucleotide tag varieties within the subset is confirmed if the multiplex polymerase chain reaction results in an amplification product; and (vi) performing, on each subset for which the presence of one or more of the oligonucleotide tag varieties was confirmed in the second screen, an individual polymerase chain reaction for each oligonucleotide tag variety within that subset, wherein each individual polymerase chain reaction comprises a primer set complementary to the first and second unique primer region of one of the plurality of oligonucleotide tag varieties, and wherein the presence of the oligonucleotide tag variety is confirmed if the individual polymerase chain reaction results in an amplification product.

In yet another embodiment, a system for identifying which of a plurality of nucleic acid tag varieties are present on an item of interest comprises: (i) a plurality of nucleic acid tag varieties, wherein each nucleic acid tag variety comprises a nucleotide-support platform attached to a nucleic acid molecule, the nucleic acid molecule of each nucleic acid tag variety comprising a first and a second universal primer region common to all nucleic acid tag varieties, and a first and a second unique primer region unique to each nucleic acid tag variety; (ii) a first primer set comprising a first primer complementary to the first universal primer region, and a second primer complementary to the second universal primer region; and (iii) a second primer set comprising a first primer complementary to the first unique primer region of one of the plurality of nucleic acid tag varieties, and a second primer complementary to the second unique primer region of the same nucleic acid tag variety.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 13 is a table depicting the results of a test for detecting and identifying deployed nucleic acid tags in accordance with an embodiment of the present invention; and FIG. 14 is a table summarizing the results of a test for detecting and identifying deployed nucleic acid tags in accordance with an embodiment of the present invention.

DETAILED DESCRIPTION OF THE INVENTION

Figure 1:
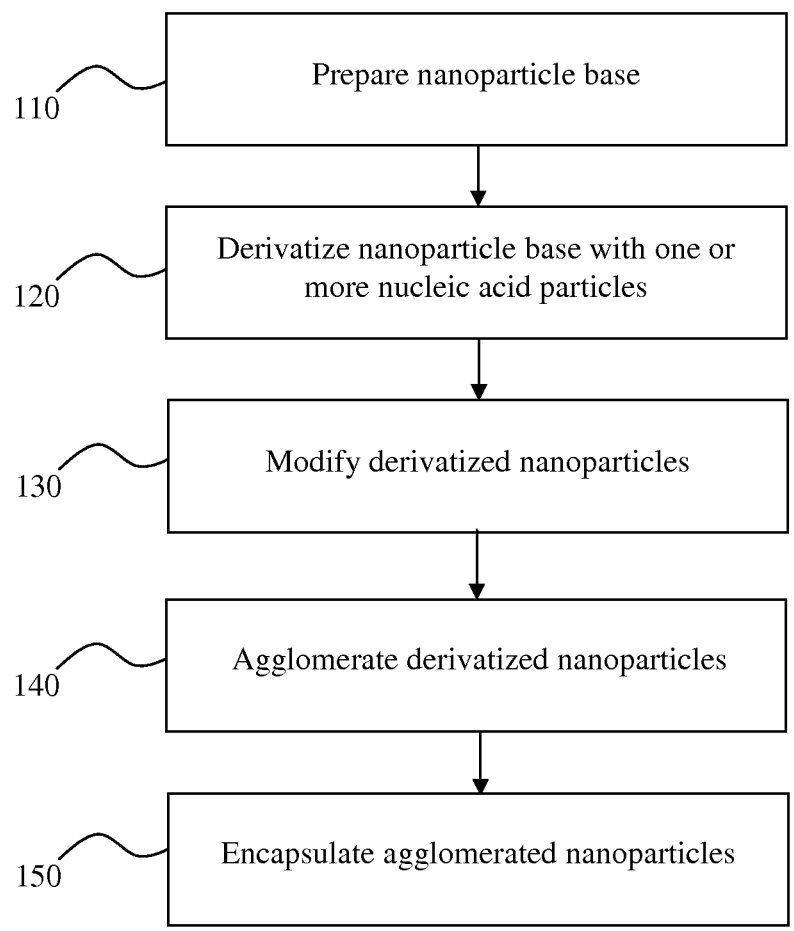
FIG. 1 is a flowchart of a process for creating a nucleic acid tag in accordance with an embodiment of the present invention.

Referring now to the drawings wherein like reference numerals designate identical or corresponding parts throughout the several views, there is shown in FIG. 1 a flowchart of an exemplary process for creating a suitable nucleic acid tag in accordance with an embodiment of the present invention. As an initial step 110, a nanometer-sized particle ("nanoparticle") platform is prepared for attachment to the nucleic acid molecule(s). A platform is used to make the nucleic acid more accessible to downstream analysis and prevent nucleic acid loss if any portion of the encapsulating layer is compromised.

The platform is any compound that can be attached to nucleic acid without unintentionally degrading or altering the nucleic acid sequence. For example, the platform can be a lightweight, durable, non-water soluble, and chemically inert structure composed of silica or polystyrene. Additionally, the nanoparticle platform should be composed of a compound that does not inhibit any downstream analysis of the nucleic acid molecules, including tag detection and polymerase chain reaction ("PCR").

At step 120, the nucleic acid molecule is attached to the prepared nanoparticle platform. The nucleic acid can be any natural or artificial nucleic acid, including but not limited to deoxyribonucleotides, ribonucleotides, oligonucleotides, nucleic acid analogs, and similar molecules that are either artificial or are otherwise found in nature, as well as combinations of any or all of the above. The nucleic acids can range from a very short sequence to a complete genome, for example. The nucleic acid molecules are optimally attached to the nanoparticle to facilitate later analysis. In a preferred embodiment, a chemical linker is used to connect the nucleic acid to the nanoparticle platform. This chemical linker must keep the nucleic acid securely tethered to the nanoparticle while avoiding inhibition of the detection or analysis of the tag and nucleic acid. Although the chemical linker can be chosen to provide a permanent covalent link between the nucleic acid and the nanoparticle platform, it could also be a compound that quickly and efficiently releases the nucleic acid at a certain temperature or after exposure to a release compound.

The nucleic acid molecule can also be designed to promote analysis. For example, to avoid steric hindrance or unwanted intermolecular interactions, the molecule can include nucleotide spacers between the chemical linker or nanoparticle base and the information-coding segment of the nucleotide sequence. Spacing between 5 and 15 bases has been optimal for current applications, although this may vary as new applications are considered.

The concentration of nucleic acid molecules on the nanoparticle platform is also an important factor in downstream analysis. If the molecules are too concentrated, steric hindrance prevents the primer and polymerase from efficiently binding the proper segments of the nucleic acid molecules. If the molecules are too sparse, the PCR signal will be diminished and can result in false negatives. In a preferred embodiment, a concentration of about $3 \times 10^{10}$ nucleic acid molecules per square centimeter is the optimal concentration for robust PCR signal.

At step 130, which can occur at the position shown in the flowchart or before or after any other step after derivatization of the nanoparticles, the derivatized nanoparticles can optionally be modified for any purpose, use, or design. For example, a flame or fire retardant can be added to the derivatized nanoparticles. The flame or fire retardant is preferably anything known by those skilled in the art to inhibit combustion or reduce the temperature of associated material in response to high temperatures, including but not limited to Nomex®, GORE-TEX®, Kevlar®, aluminum hydroxide, magnesium hydroxide, hydromagnesite, calcium silicate, or halocarbons, among many others. While some compounds provide the tag with resistance to combustion, others provide the tag with thermal protection by absorbing heat in an endothermic reaction, through chemical degradation, or by otherwise protecting the tag from high temperatures.

The derivatized nanoparticles can also be modified to include an odorant. The odorant can be anything known to be capable of detection by mechanical means or by human or animal means (i.e., olfaction detection). The odorant can comprise anything known by those skilled in the art to be capable of detection, including a single aromatic, a blend of aromatics, or a commercially available synthetic chemical, among many others. Since the surfaces on which the odorant might be detected will vary, the odorant will preferably be unique or distinctive enough to be detected over random odorants present on these surfaces or in the surrounding environment. Although according to one embodiment the odorant is capable of detection by humans and/or animals, in the preferred embodiment the odorant can only be detected by animals and/or electronic means, thereby evading human detection. For example, mechanical means such as an "electronic nose" could be programmed or trained to recognize the odorant and alert the user to its presence. In a preferred embodiment, the sensor provides quantitative information about detection and is sensitive enough to detect very minute or trace amounts of the odorant.

Lastly, the tag can also be modified with other compounds to provide additional desired characteristics including but not limited to color, luminescence, or protection against ultraviolet radiation.

At step 140 of the exemplary method, the nucleic acid-derivatized nanoparticles are agglomerated. Agglomeration protects the nucleic acid molecules from degradation and facilitates encapsulation. To agglomerate the particles to the desired size range, the nanoparticles are vacuum dried, milled, and sieved.

Compounds might be used or incorporated into the tag to promote disagglomeration of the agglomerates prior to PCR analysis. These compounds might be bovine serum albumin, salmon sperm DNA, carbohydrates, polyvinyl alcohol, fructose, or chitosan, among others. With more nucleic acid exposed during dissolution, subsequent analysis will be faster and more sensitive.

After the nanoparticles are agglomerated, the agglomerates are encapsulated at step 150. The encapsulant protects the nucleic acid from degradation by ultraviolet light, hydrolysis, enzymatic digestions, chemical degradation, or any other means. Additionally, the encapsulant can be designed such that it does not hinder analysis of the nucleic acid molecules. For example, the encapsulant should not contain any compounds that would inhibit or prevent a PCR reaction, although efficient removal of the encapsulant before PCR analysis would eliminate this requirement. Additionally, the encapsulant should enhance the ability of the tag to discretely attach to people and objects. If covertness is required, the encapsulant can be designed to deter detection.

The encapsulating layer can also be designed with surface moieties added to the inner or outer surfaces of the encapsulant or incorporated into the encapsulant material. The moieties are designed to facilitate a particular use of the nucleic acid tag. For example, the moiety can be hydrophobic to enable stickiness or contain antibodies designed for specific targeting. The molecular interactions between the moiety and a target compound can range from simple electrostatic interactions to antibody-antigen recognition. The moiety can also promote detection of the nucleic acid tag.

To protect the nucleic acid from degradation, the encapsulating layer can be coated with or include another functional layer of material. For example, the encapsulant can be coated with or include a non-water-soluble compound to prevent access to water or similar molecules. The encapsulant can also be coated with or include a UV-blocking compound such as titanium dioxide to prevent UV-induced degradation of the nucleic acid molecules.

In yet another embodiment, the nucleic acid tag comprises just nucleic acid, or nucleic acid in combination with a structure or base other than a nanoparticle. For example, the nucleic acid may be unencumbered, or it may be tethered (covalently or non-covalently) to a structure or base. There may be many copies of the nucleic acid, or just a few copies, and can range from a very short sequence to a complete genome, for example. The nucleic acid can be connected to the structure or base by a chemical linker. Although the chemical linker can be chosen to provide a permanent covalent link between the nucleic acid and the structure or base it could also be a compound that quickly and efficiently releases the nucleic acid at a certain temperature or after exposure to a release compound. The nucleic acid molecule can also include nucleotide spacers between the chemical linker or nanoparticle base and the information-coding segment of the nucleotide sequence in order to avoid steric hindrance or unwanted intermolecular interactions. Spacing between 5 and 15 bases has been optimal for current applications, although this may vary as new applications are considered.

Figure 2:
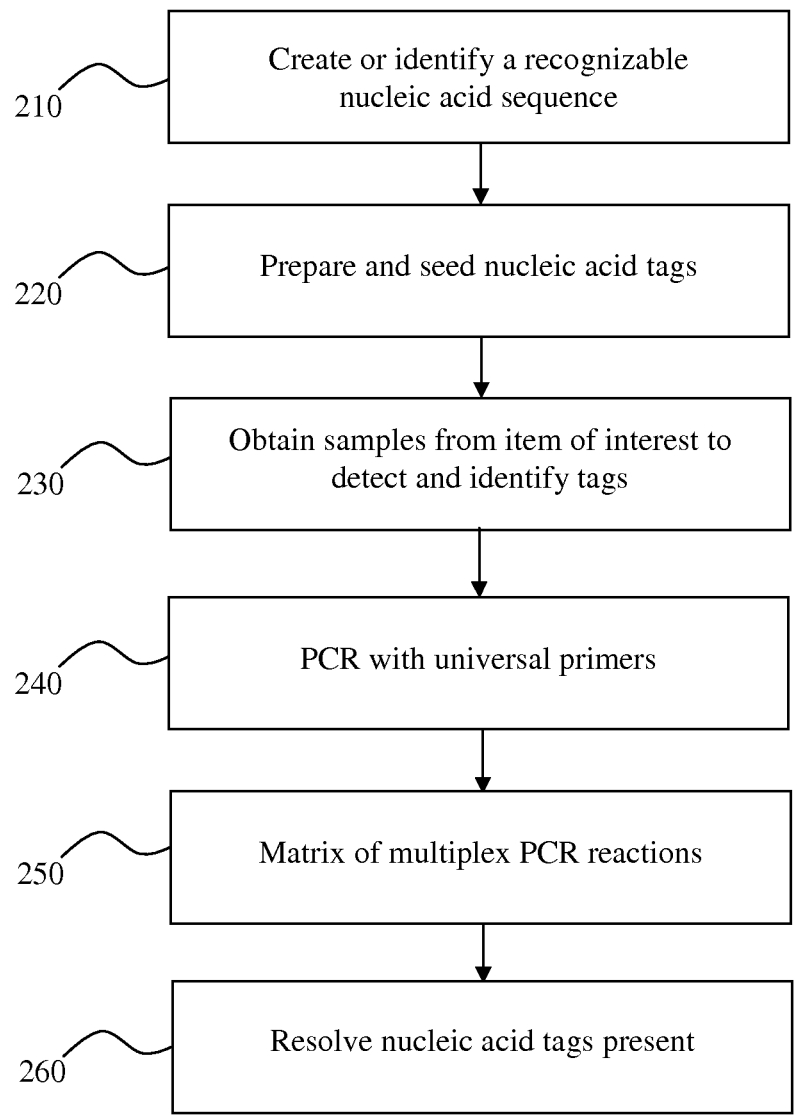
FIG. 2 is a flowchart of a process for detecting and identifying deployed nucleic acid tags in accordance with an embodiment of the present invention.

FIG. 2 is a schematic representation of an embodiment of a detection and identification method according to the present invention. More specifically, the figure represents a method for detecting the presence of one or more deployed nucleic acid tags, and then identifying which of a plurality of different nucleic acid tags are present.

As an initial step 210, a suitable nucleic acid sequence is characterized or created. In one embodiment of the present invention, the sequence ranges from a short oligonucleotide to an entire genome and is generated through any of the various known methods of natural or artificial nucleic acid synthesis. The nucleic acid can be completely composed of either natural nucleic acids which normally compose the genomes of organisms, artificial nucleic acids, or any combination thereof.

In a preferred embodiment, the nucleic acid molecules contain primer-binding sequences surrounding unique nucleotide sequences. The unique nucleotide sequence contained between the primers can encode information that corresponds to an identification, location, date, time, or other data specific to that unique sequence. Since analysis of every nucleic acid molecule can use the same primers, the analysis can be performed faster and more efficiently.

The primer sequences, whether they are unique or identical for each location or use, are chosen to avoid cross-reactions with naturally-occurring nucleic acid molecules in the environment in which the nucleic acid is located. Although only a fraction of natural nucleic acid molecules on Earth have been characterized by scientists, the search of nucleic acid repository databases such as GenBank®, the National Institutes of Health database containing all publicly available DNA sequences, could be a preliminary step in constructing the primer sequences.

In one embodiment of the current invention, unique groupings of nucleotides are assigned a specific letter, number, or symbol value in order to encode information within the sequence. By placing the unique groupings in order, information can be encrypted into the nucleotide sequence. To further increase the security of the information, advanced encryption algorithms can be used to assign letter, number, or symbol values to specific nucleotides or nucleotide groupings. Additionally, the encryption system can be periodically changed to prevent decryption by intercepting entities.

The nucleic acid can also be encoded to contain information other than a string of letters, numbers, and symbols. For instance, the sequence can be a random sequence that corresponds to the item, location, or date that the object of interest will be seeded. Alternatively, the tag can be as simple as a single nucleic acid change in a previously identified or known sequence. For example, the nucleotide sequence can be embedded in a full or partial genomic sequence corresponding to an organism which naturally exists in the location to be seeded. Modifications to the natural nucleic acid sequence, known only to the creator of the tag, can be made such that the changes resemble natural variations of the sequence and thus fail to arouse suspicion, even by individuals that might suspect such tags are present.

To decrypt the encoded information according to this system, an individual will need: (1) knowledge that encoded nucleic acid is present; (2) knowledge of the specific location of the information within the nucleic acid in order to use the appropriate primers for amplification and sequencing reactions; (3) access to a PCR machine and reagents; and (4) the encryption algorithm, or, alternatively, complex decryption capabilities.

Although creating the nucleic acid target within the genome of an naturally-occurring organism provides numerous benefits, both in vivo and in vitro DNA replication occasionally introduces random errors into a DNA sequence despite the actions of proof-reading and repair enzymes. By deleting one or more nucleotides or frame-shifting the nucleic acid sequence, these mutations can disrupt any encrypted information contained therein. Computer algorithms are used to restore the information by recognizing and repairing the errors. For example, if a mutation adds one or more nucleotides to a pre-defined sequence and disrupts the information, the algorithm removes single or multiple nucleotides from the sequence until the information is corrected. Similarly, if a mutation removes one or more nucleotides, the algorithm systematically adds nucleotides to the sequence until the information is corrected. The algorithm must also be robust enough to decrypt sequences that contain more than one type of error-inducing mutation, and must be capable of recognizing when the information contained with the nucleic acid has been restored.

In step 220 of the exemplary method shown in FIG. 2, the nucleic acid is packaged, prepared, or otherwise modified prior to use. Preparation of the nucleic acid can range from little or no preparation or modification to an extensive series of steps for modifying the nucleic acid. For example, the nucleic acid can be used to derivatize nanoparticles, as described above, or can be added to another structure or base.

Figure 3:
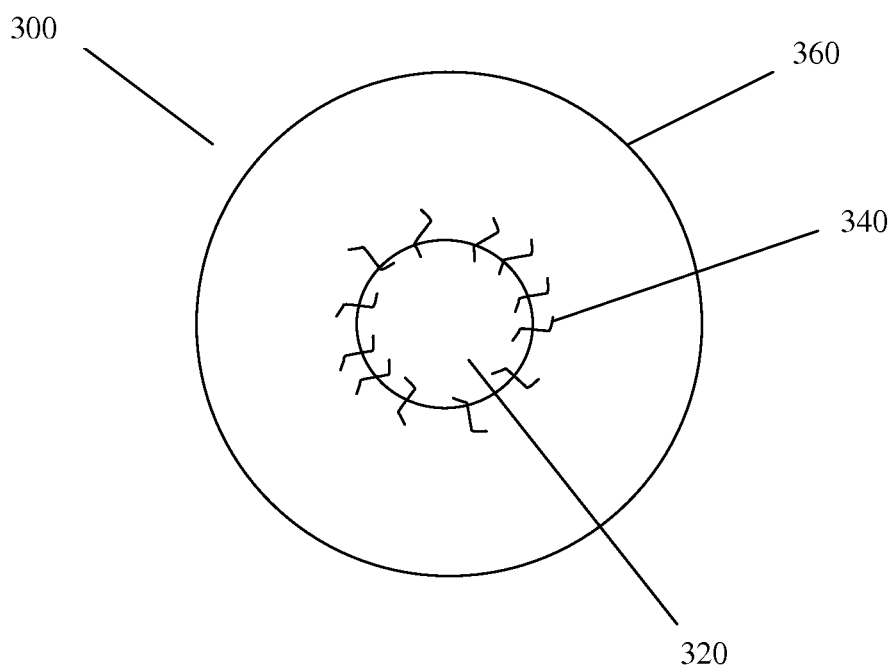
FIG. 3 is a side view of a nucleic acid tag complex in accordance with an embodiment of the present invention.

As another example, the nucleic acid can be packaged into an appropriate tag complex. To avoid potentially harmful environmental side-effects, the tag can be large enough to avoid being inhaled by people or organisms but small enough to be covert. FIG. 3 represents one embodiment of this tag structure. Tag 300 is composed of a single nucleotide-support platform 320, nucleic acid 340, and encapsulant 360.

Figure 4:
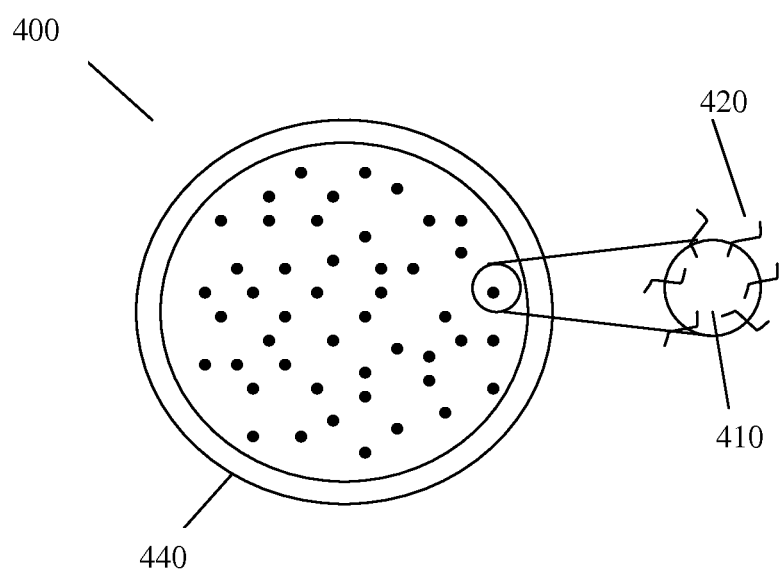
FIG. 4 is a side view of encapsulated nucleotide-derivatized nanoparticles in accordance with an embodiment of the present invention.

FIG. 4 is a side view of another embodiment of a tag structure. Tag 400 is composed of nucleotide-support platform 410 derivatized with nucleic acid 420 and surrounded by encapsulant 440. Similar to the tag in FIG. 3, tag 400 contains nucleic acids that are contained within an encapsulant that protects the sequence without inhibiting later analysis. Unlike the bead platform used by the tag in FIG. 3, nucleotide-support platform 410 is composed of nanoparticles. Tag 400 can contain thousands, millions, or even billions of nucleotide-derivatized nanoparticles within the encapsulant layer.

In yet another embodiment, the tag complex can be modified to include, comprise, or be associated with an additional element 500 such as a unique identifier, a fire or flame retardant, a UV-protectant, a waterproof element, and/or an odorant, among many other types of modification. For example, a fire or flame retardant can protect the tag by resisting combustion or lowering high external temperatures. A fire- or high temperature-resistant tag can be used for many different applications, including those where the tag is expected to be exposed to fire or the high temperature of an explosion. The tags can be used to detect tampering in areas or on items or individuals suspected to be involved in the constructions of bombs or other incendiary devices, and the fire- or heat-resistant element would help the tamper tag survive the explosion, which could then be analyzed using downstream processes.

Figure 5:
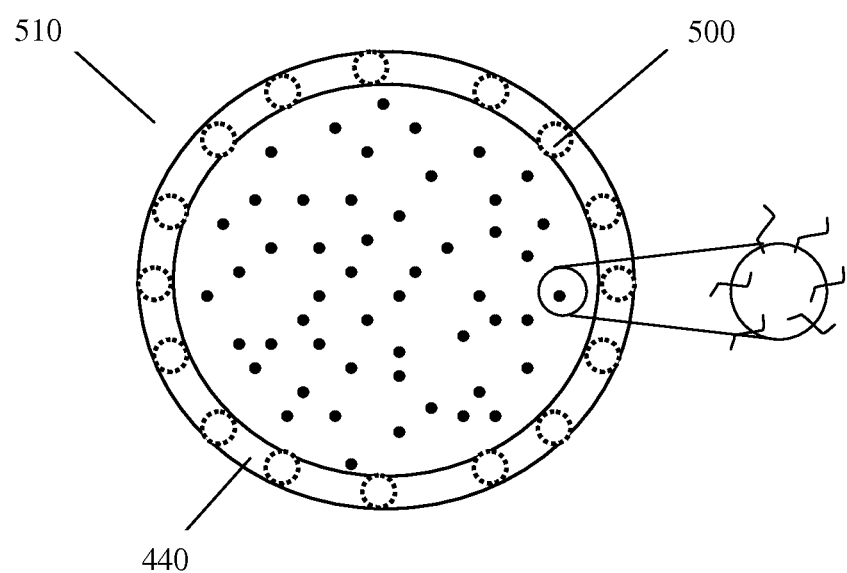
FIG. 5 is a side view of an encapsulated nucleotide tag complex with marker elements incorporated into the encapsulant layer in accordance with an embodiment of the present invention.
Figure 6:
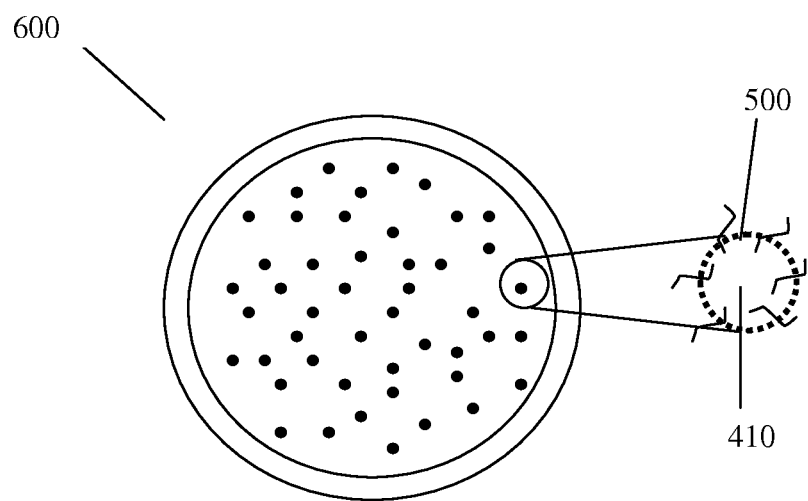
FIG. 6 is a side view of an encapsulated nucleotide tag complex with marker elements incorporated into the nanoparticles in accordance with an embodiment of the present invention.
Figure 7:
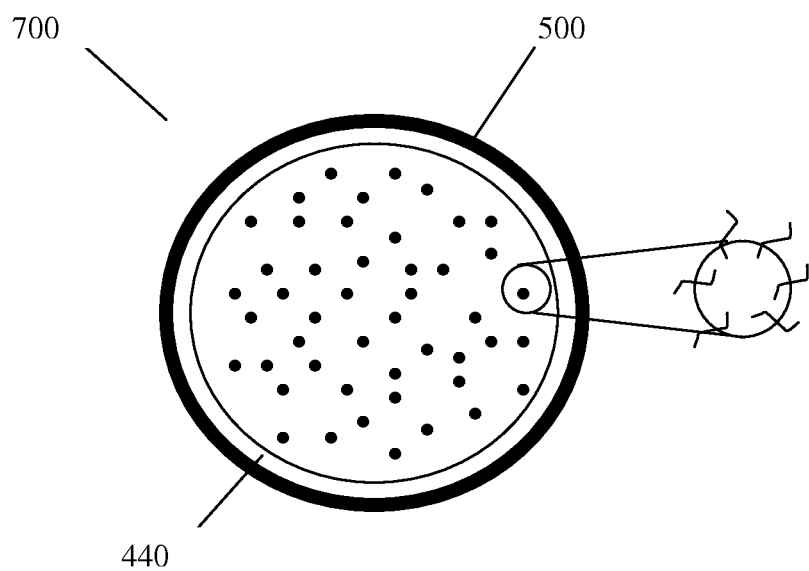
FIG. 7 is a side view of an encapsulated nucleotide tag complex with marker elements coating the outer surface of the encapsulant in accordance with an embodiment of the present invention.
Figure 8:
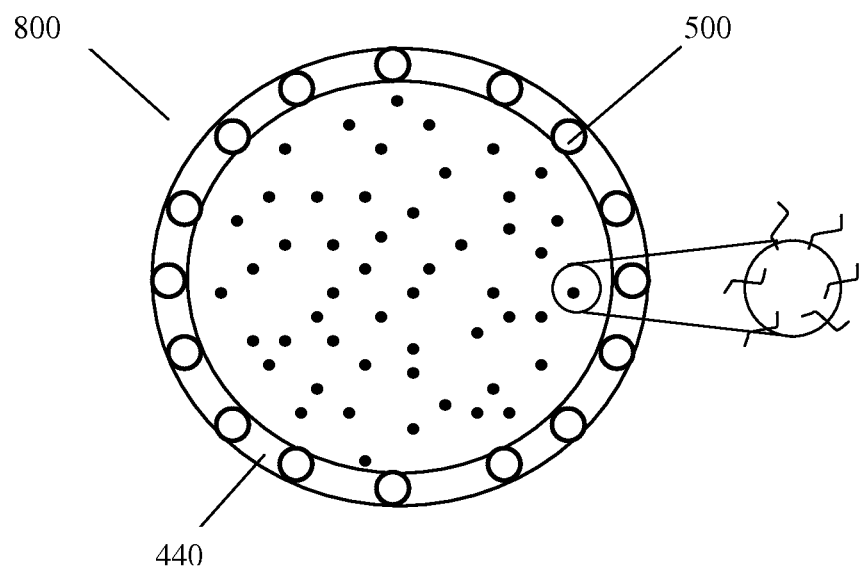
FIG. 8 is side view of an encapsulated nucleotide tag complex with marker elements coating the outer surface of the encapsulant in accordance with an embodiment of the present invention.
Figure 9:
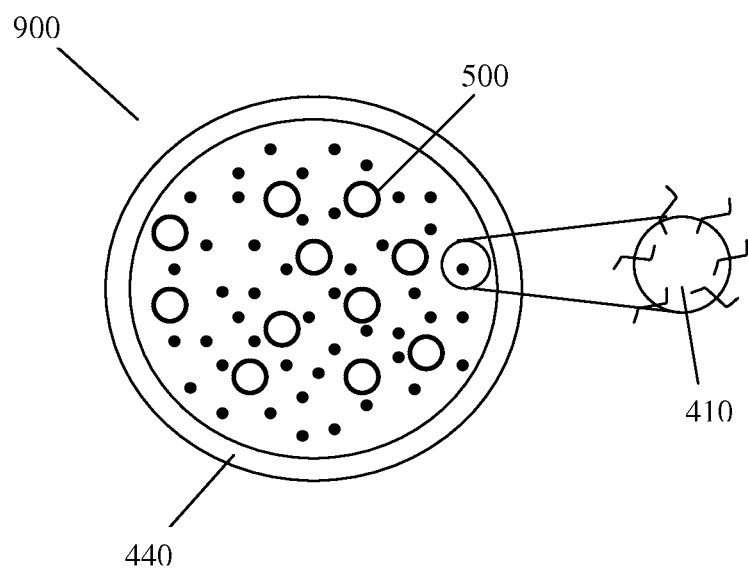
FIG. 9 is a side view of an encapsulated nucleotide tag complex with marker elements trapped inside the tag by the encapsulant layer in accordance with an embodiment of the present invention.

Additional element 500 can be incorporated into the tag in a number of different ways. For example, in FIG. 5 additional element 500 is incorporated into encapsulant 440 around tag 510. In FIG. 6, additional element 500 forms a portion of the structure or base 410 that the nucleic acid is bound to. In FIG. 7, additional element 500 forms a layer on the exterior surface of encapsulant 440. In FIG. 8, additional element 500 is incorporated into the exterior layer of tag 440. In FIG. 9, additional element 500 is separate from nucleotide-support platform 410 and encapsulant 440 but is trapped within the interior of tag 900.

While the embodiments depicted in FIGS. 5-8 are shown with nucleic acid derivatizing a nanoparticle, the nucleic acid may be unencumbered, or may be attached or in communication with another form of structure or base. None of these embodiments are meant to limit the potential scope of the invention, or fully describe the possible combinations of nucleic acid, support platform, and additional elements.

At step 220 of the exemplary method depicted in FIG. 2, an item, object, person, or area of interest is seeded with the prepared or packaged nucleic acid. The nucleic acid could simply be placed on or bound to an item or in an area, or a more complicated form of inserting, planting, or seeding the nucleic acid could be used. The nucleic acid can be placed or seeded by hand, or can be placed or seeded using mechanics or an automated process, or a combination of methods can be used. At step 230 of the method, a person, container, item, or object of interest is later examined for the presence of the nucleic acid. For example, a labeled item may be examined to determine the authenticity of that item, and whether there has been a substitution or tampering. As another embodiment, a labeled item may be examined to determine whether it has passed or traveled through an area that was previously seeded with nucleic acid tags. Many other scenarios are possible.

If the seeded nucleic acid contains, comprises, or was distributed in connection with retroreflectors, electromagnetic waves can be used to detect the presence of seeded nucleic acid. Scanning equipment shines light on the object of interest and looks for a wave front that is reflected along a vector that is parallel to but opposite in direction from the wave's source. This suggests that retroreflective tags are present on the exterior of the object and alerts the authorities that further investigation is necessary. This rapid and cost-effective identification of retroreflective tags is especially useful for high-throughput locations such as checkpoints and border crossings. Once the retroreflective tags are detected, they can be removed from the surfaces of the object for analysis of the attached nucleic acids to identify geographic locations.

The nucleic acid can also contain, comprise, or be seeded in connection with luminescent compounds that reveal their presence from a distance. Although the preferred embodiment uses fluorescent or phosphorescent photoluminescence, other embodiments may include chemiluminesent, radioluminescent, or thermoluminescent compounds. The photoluminescent compound is chosen such that absorption of a photon with a certain wavelength by the compound causes the emission of a photon with a different wavelength. The difference between the wavelength of the absorbed photon and the wavelength of the emitted photon depends on the inherent physical properties of the chosen compound.

In the preferred embodiment, the luminescent compound absorbs and emits photons in the ultraviolet band—between 400 and 10 nanometers—of the electromagnetic spectrum. The compound is chosen to avoid interference by UV radiation from the sun. The Earth's atmosphere absorbs as much as 99% of the UV radiation emitted by the sun in the 150-320 nm range. Thus the most advantageous luminescent compound absorbs and emits photons with wavelengths below 320 nm.

As an alternative to luminescent compounds that absorb and emit photons in the 150-320 nm range, compounds that absorb and emit photons of wavelengths greater than 320 nm can be used under certain circumstances. For example, these compounds could be used during nighttime conditions or in an enclosed UV-blocking environment such as a windowless structure.

The luminescent compound can be incorporated into the nucleic acid or the support platform in a number of different ways. For example, the compound can be entirely separate from the nucleic acid or the support platform. The compound can form a layer on the exterior surface of the nucleic acid or the support platform. The compound could also coat the interior surface of the encapsulant, or be incorporated into the encapsulant. In several of the described embodiments, the encapsulant layer must be designed to prevent inhibition of excitation and emission wavelengths.

If the seeded nucleic acid or support platform contains a photoluminescent compound, electromagnetic waves can be used to detect the presence of the tags at a distance. Scanning equipment shines photons of the excitatory wavelength on the object of interest and looks for photons emitted at the proper wavelength as determined by the compound used in the tags. Detection of photons with the correct wavelength suggests that a nucleic acid-labeled tag is present and alerts the scanner that further investigation is necessary. The advantage of this system is that the scanning equipment and tag can be designed such that the individual doing the scanning does not have to be in close proximity to the object of interest.

The detection process can be automated. An individual or object of interest can be forced to travel through a scanning point containing excitation equipment and emission detection equipment. As the individual or object of interest travels through the scanning point, the equipment scans for emitted photons of a certain wavelength. When the emitted photons are detected, a computer at the scanning point automatically alerts a remotely-located entity that subsequent analysis is necessary.

In yet another embodiment of the current invention, the detected nucleic acids taken from the item of interest are analyzed using any method that determines the exact order of nucleotide bases. There are currently a number of different commonly-used sequencing techniques including but not limited to dye-terminator sequencing, parallel sequencing, and sequencing by ligation. Sequencing machines allow automated sequencing and can be run 24 hours a day. If PCR techniques are used, the appropriate primers are chosen based upon the types of nucleic acid and/or tags known to be in the location of interest. Prior to sequencing or amplification, it is necessary to dissolve or otherwise remove an encapsulant layer from the tag in a manner that avoids inhibition of the downstream sequencing or PCR reactions, if such a layer is present or suspected to be present. In one embodiment, the encapsulant and/or agglomerate is disrupted by bead beater, a form of mechanical disruption. This one-step method avoids chemicals or extractions which could affect or inhibit PCR reactions.

In addition to the traditional sequencing techniques described above, real-time PCR and sequencing by hybridization techniques allow detection of target nucleic acids. According to the real-time PCR technique, the extracted nucleic acid is placed into a well or tube that has been pre-loaded with all reagents necessary for a PCR reaction as well as a sequence-specific, nucleotide-based, fluorescently-labeled probe. As the extracted nucleic acid is amplified, the polymerase degrades the probe and releases the fluorescent reporter. The reporter immediately fluoresces and alerts the system to the presence of a nucleotide. Under the sequencing by hybridization technique, the extracted nucleic acid is labeled with a fluorescent marker and is hybridized to a DNA microarray that contains the complementary nucleotide sequence from known seeded nucleic acid. If the extracted nucleic acid hybridizes to any of the complementary nucleic acid, the fluorescent signal alerts the system to the presence of a target nucleic acid.

However, under current methods and systems for detecting and identifying different nucleic acid tags, a sample is obtained from an object of interest, which may or may not have been labeled with or picked up deployed nucleic acid tags. The samples are then brought to a laboratory or analysis center to identify the specific tags that have labeled the object, potentially through a mechanism such as quantitative real-time polymerase chain reaction ("qrt-PCR"). Consequentially, a sample from an object must be tested for each individual tag. If there are twenty tags that potentially label an object, each sample from the object requires twenty PCR tests to identify which tags labeled the object. This approach presents several challenges to the rapid detection and identification of multiple tags from samples.

First, an object of interest will almost certainly not be labeled uniformly. Multiple samples from the object are needed to detect all tags labeling the object. Testing multiple samples from each object increases the time and work required to accurately identify the tags labeling an object. One test to detect a single DNA tag sequence from start to finish requires approximately 35 minutes, and more if sample preparation is needed. If twenty tags are suspected on an object and ten samples were collected, determining the identity of tags on the object would require 200 individual tests, sequentially over 4.5 days of continuous lab testing. While running the tests in parallel will reduce the time required for analysis, it does not reduce the number of overall tests or the costs of reagents, for example.

Second, environmental contaminants collected with the samples cause the tags to degrade over time. Samples must be tested soon after being collected from an object to have the highest likelihood of correctly identifying all tags in the sample. To address the need to efficiently perform a large number of tests, the use of nested PCR and a matrix-based multiplex PCR approach to tag detection and identification is proposed.

Figure 10:
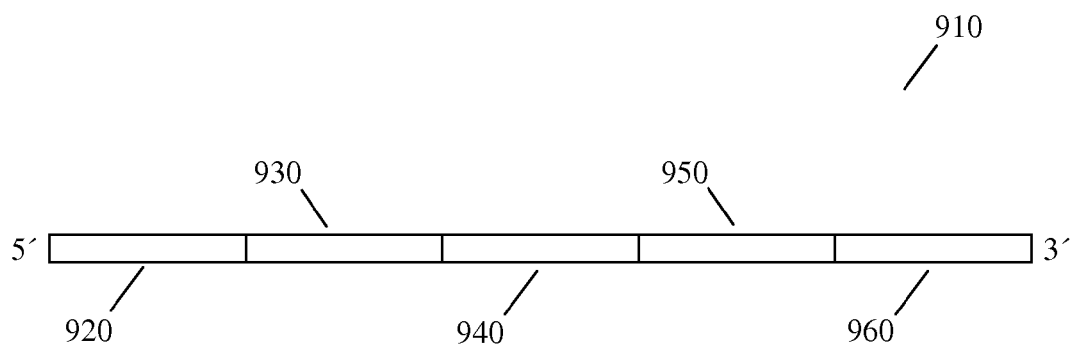
FIG. 10 is a schematic representation of a nucleic acid in accordance with an embodiment of the present invention.

Under this approach, diagram of which is shown in FIG. 10, each nucleic acid tag 910 is designed to include an identical primer recognition region of nucleotides at the beginning and end of the tag (i.e, a flanking universal primer), an inner set of tag specific primer recognition regions 930 and 950, and a spacer of random nucleic acid unique to each tag 940.

The tag design depicted in FIG. 10 enables nested PCR, in which all samples would first be subjected to PCR using the universal primers, as shown at step 240 of the method in FIG. 2. PCR with the universal primers allows any sample containing tag to be detected. Amplification with the universal primers is a positive confirmation of one and potentially multiple tags being present, though the specific tags are unknown.

These amplified samples are then subjected to a matrix of multiplex PCR reactions to determine the individual tags present, as shown at step 250 of the method in FIG. 2. The matrices of reactions are designed to detect specific tag groups, rather than individual tags. A group that indicates the positive presence of at least one tag is then further tested to determine the exact tags that are present in the sample. With this multiplex approach, a sample will undergo PCR with multiple primer sets (all of the primers for the tags in the group). If amplification is detected, the sample is subjected to additional reactions where the individual primers in the group are tested separately, or depending on the group size, the groups can be split again into smaller groups and tested again. This process can be repeated until the individual targets are resolved. The following is an example of this approach.

In one application, one or more parameters of the matrix of multiplex PCR reactions—as well as the results of those reactions—are determined and/or analyzed by an automated process such as a computer program. Although the example provided below uses a total of 20 different potential tags, the number of potential tags could be orders of magnitude larger. With a large number of potential tags, there would be a need software that could determine which primer sets to use in each of the multiplex reactions in order to maximize results with the minimum number of PCR reactions. The software could also review the results and recommend (or automatically perform, depending upon the presets of the software and/or needs of the user) the next step(s) in the analysis, including but not limited to parameters such as primer sets, PCR settings, groupings, or any other parameter mentioned, suggested, or made obvious by the specifications herein. Such software would be within the knowledge of one of skill in the art.

Example 1

Figure 11:
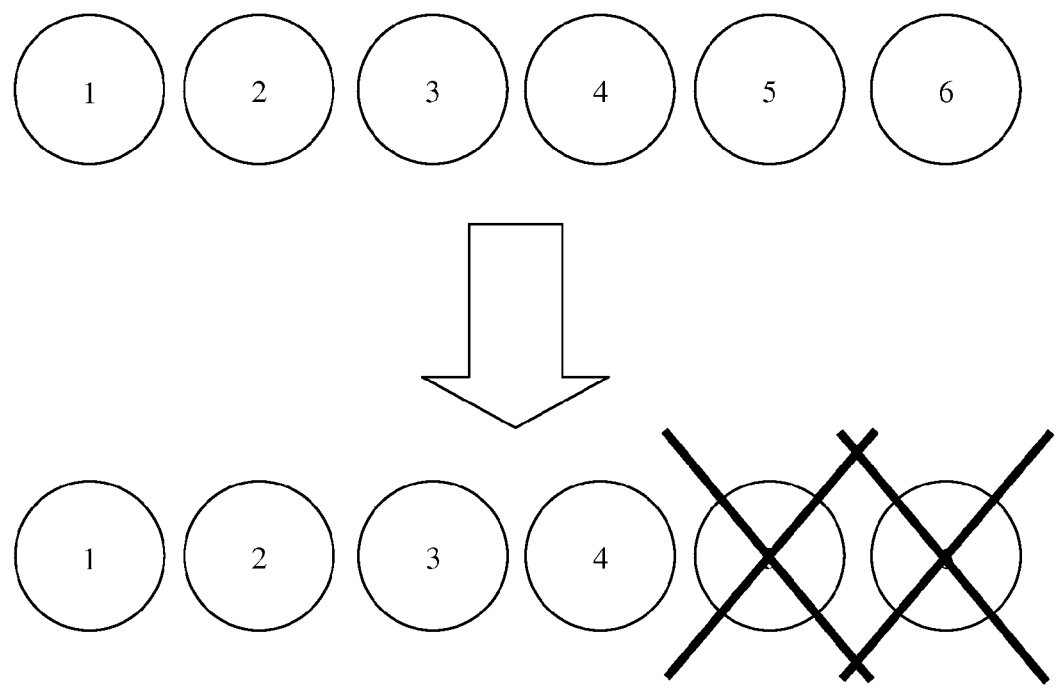
FIG. 11 is a schematic representation of a step in a method for detecting and identifying deployed nucleic acid tags in accordance with an embodiment of the present invention.

An object of interest has been received. It is known the number of potential tags labeling the object is 20. Six samples are taken from the object. Using current methods, there are 120 tests that need to be performed to determine all of the tags that have possible labeled the object. Using the proposed approach the universal primer PCR test is done on the six samples. Two of the samples do not indicate the presence of any tag, as shown in FIG. 11. At this point there have been six tests with the six samples tested for the universal primer. Two of the samples have been ruled out.

Figure 12:
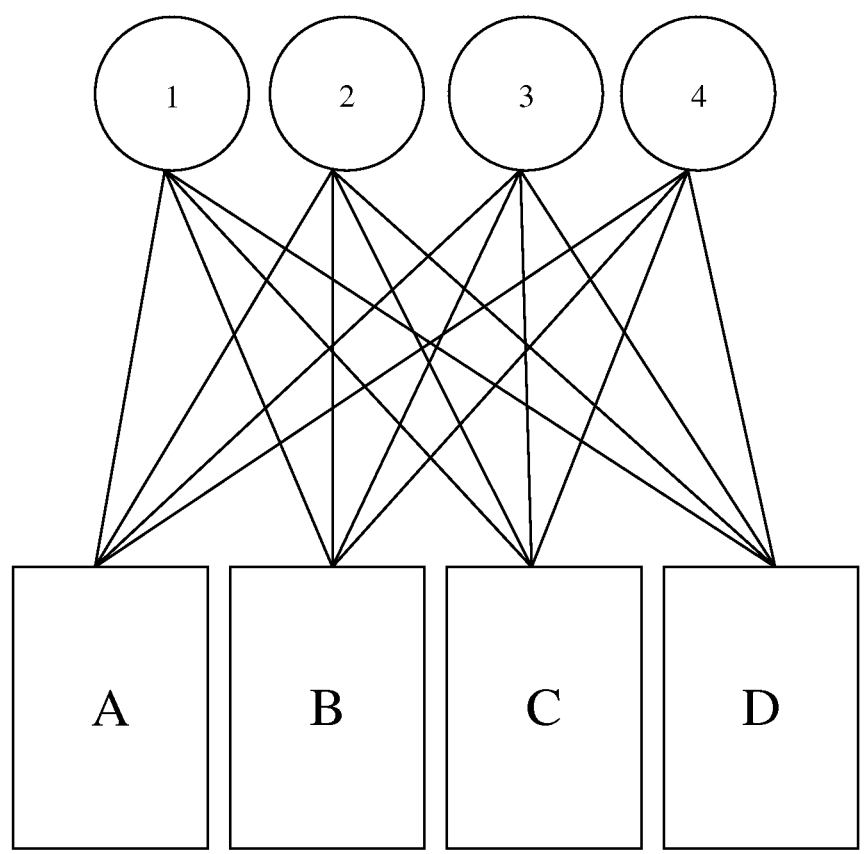
FIG. 12 is a schematic representation of a step in a method for detecting and identifying deployed nucleic acid tags in accordance with an embodiment of the present invention.

Next is the multiplex PCR step, as shown in FIG. 12, in which the remaining four samples are tested with four sets of primer reactions, labeled A through D. Each set of primer reactions consists of five tag primers: A comprises tag-specific primers for tags 1-5; B comprises tag-specific primers for tags 6-10; C comprises tag-specific primers for tags 11-15; and D comprises tag-specific primers for tags 16-20. If there were more possible tags seeded, there could be more possible primer reactions (E with primers for tags 21-25; F with primers for tags 26-30, etc.). The test count is now six initial tests plus four samples each tested four times for a total of 22 tests performed to this point.

The results of the multiplex step in this example, as shown in the table in FIG. 13, find that Sample 1 is positive for each of the four multiplex tests. Samples 2 and 4 were positive in two of the tests, and sample 3 was positive in one of the tests.

Now, individual tags tests can be performed per the table shown in FIG. 14, which summarizes the results from FIG. 13. The total number of tests required has already been significantly reduced. Since Sample 1 was positive in all multiplex tests, it is first tested for all 20 potential tags. If Sample 1 is found to contain all 20 tags no further testing would be needed. If this is not the case, Sample 2 is then tested for any tags 6-15 that Sample 1 tested negative. The process continues until all samples & tags have been positively confirmed or determined to be absent from the object.

Thus, if any of the tags 1-20 are not detected during the analysis of Sample 1, then the other samples would be tested to determine whether or not the tag(s) not found in Sample 1 labeled the object. For example, if Sample 1 tests negative for tags 2, 8, 16, 17 and 19, then Sample 2 is tested for tag 8, Sample 3 is tested for tag 2 and Sample 4 is tested for tags 2, 16, 17, and 19. This completes the testing needed to determine all the tags that have labeled the object of interest. The 120 possible test has been shortened to 48 tests (6+16+20+6), a reduction of almost 60%.

This example highlights an average case. If, in the multiplex PCR step, all the samples show positive results in all the tag groups then the samples could be tested sequentially to realize a slight savings in number of tests to complete. In the worst case, sample 1 would be positive for only 1 tag in each group, and Sample 2 would need to be tested for the remaining 16 tags. In the worst case scenario, sample 2 would be negative for all 16 tags and Sample 3 would then be tested for all 16 tags. Assuming the worst case, sample 3 would be negative for all 16 tags, and sample 4 would then be tested for all 16 remaining tags. In total, 90 tests (6+16+20+16+16+16) would need to be run in the example where the first universal primer test ruled out two samples but the four remaining samples were positive. This is still an improvement over 120 tests. And, in the absolute worst case, where all 6 samples are positive in the universal PCR tests and all samples are positive in the multiplex step, the total number of tests in a worst case scenario would be 6+24+20+16+16+16+16+16=130 tests; an additional 10 tests have been performed. This is approximately 10% more tests than would have been needed.

One major benefit in the nested PCR approach is realized in the field. A single test that takes as few as 35 minutes will quickly indicate whether or not an object is tagged. The results could support real-time infield decisions that would not be possible without the knowledge. This ability limits the amount of time sample collectors would invest in a single object that may or may not be tagged. If the samples do not show tag, the samples would not need to be shipped to a more permanent laboratory for further investigation. Another benefit of the nested PCR approach is the rapid expansion of the amount of DNA available for analysis for each sample. The amplicons of this first PCR step would contain orders of magnitude more individual tag than the original sample contained, due to the nature of PCR. The PCR product would contain so many individual tags that they would need to be diluted to be further tested in the multiplex steps. The increase of target material increases sensitivity of further tests.

The multiplex PCR can be utilized for additional information. For example, the multiplex tag groups can be created to reflect geographic locations. In the above example tags 1-5 could all be tags from the northwest quadrant of a city. This would allow, with only two sets of tests, to determine the object was in that quadrant of the city. No further testing is necessary if that is all the resolution that is needed.

The method presented addresses two problems in DNA labeling; it reduces the number of PCR tests that are needed to resolve multiple tags from a single object; and it allows for rapid tag identification, thereby eliminating the need to continuously test samples that do not contain tags.

Although the present invention has been described in connection with a preferred embodiment, it should be understood that modifications, alterations, and additions can be made to the invention without departing from the scope of the invention as defined by the claims.

What is claimed is:

1. A method for identifying which of a plurality of nucleic acid tag varieties are present on an item of interest, the method comprising the steps of:
    creating a plurality of nucleic acid tag varieties, wherein each nucleic acid tag variety comprises a nucleotide-support platform attached to a nucleic acid molecule, the nucleic acid molecule of each nucleic acid tag variety comprising a first and a second universal primer region common to all nucleic acid tag varieties, and a first and a second unique primer region unique to each nucleic acid tag variety;
    deploying the plurality of nucleic acid tag varieties in a plurality of locations, wherein a single one of the plurality nucleic acid varieties is deployed in a distinct one of the plurality of locations;
    receiving samples from the item of interest, wherein the object has traveled through at least one of the plurality of locations after deployment of the nucleic acid tag varieties;
    performing a first screen of each of the samples with a polymerase chain reaction comprising a primer set complementary to the first and second universal primer regions, wherein the presence of one or more of the plurality of nucleic acid tag varieties is confirmed if the polymerase chain reaction results in an amplification product; and
    performing, on each of the samples for which the presence of one or more of the plurality of nucleic acid tag varieties was confirmed in the first screen, a second screen comprising a series of multiplex polymerase chain reactions, wherein each multiplex polymerase chain reaction comprises a primer set complementary to the first and second unique primer regions of a subset of two or more of the plurality of nucleic acid tag varieties, and wherein the presence of one or more of the nucleic acid tag varieties within the subset is confirmed if the multiplex polymerase chain reaction results in an amplification product.

2. The method of claim 1, further comprising the step of performing, on each subset for which the presence of one or more of the nucleic acid tag varieties was confirmed in the second screen, an individual polymerase chain reaction for each nucleic acid tag variety within that subset, wherein each individual polymerase chain reaction comprises a primer set complementary to the first and second unique primer region of one of the plurality of nucleic acid tag varieties, wherein the presence of the nucleic acid tag variety is confirmed if the individual polymerase chain reaction results in an amplification product.

3. The method of claim 1, wherein each nucleic acid tag variety further comprises a nucleic acid spacer unique to each tag and disposed between said first and second unique primer region.

4. The method of claim 1, wherein the nucleic acid molecule is composed of nucleotides selected from the group consisting of ribonucleotides, deoxyribonucleotides, nucleotide analogues, and mixtures thereof.

5. The method of claim 3, wherein the nucleic acid molecule is an oligonucleotide.

6. The method of claim 1, wherein the nucleic acid molecule is genomic deoxyribonucleic acid ranging from two nucleotides to the entire genome.

7. The method of claim 1, wherein information about the item of interest is contained within the nucleic acid molecule.

8. The method of claim 2, further comprising the step of sequencing the amplification product of one or more of the polymerase chain reactions.

9. The method of claim 1, wherein the nucleotide-support platform is a nanoparticle.

10. The method of claim 1, wherein each nucleic acid tag variety is encapsulated by an encapsulant.

11. A method for identifying which of a plurality of oligonucleotide tag varieties are present on an item of interest, the method comprising the steps of:
    creating a plurality of oligonucleotide tag varieties, wherein each oligonucleotide tag variety comprises a nanoparticle nucleotide-support platform attached to a oligonucleotide, the oligonucleotide of each oligonucleotide tag variety comprising a first and a second universal primer region common to all oligonucleotide tag varieties, a first and a second unique primer region unique to each oligonucleotide tag variety, and a nucleic acid spacer unique to each oligonucleotide tag and disposed between said first and second unique primer regions;
    deploying the plurality of oligonucleotide tag varieties in a plurality of locations, wherein a single one of the plurality nucleic acid varieties is deployed in a distinct one of the plurality of locations;
    receiving samples from the item of interest, wherein the object has traveled through at least one of the plurality of locations after deployment of the nucleic acid tag varieties;

performing a first screen of each of the samples with a polymerase chain reaction comprising a primer set complementary to the first and second universal primer regions, wherein the presence of one or more of the plurality of oligonucleotide tag varieties is confirmed if the polymerase chain reaction results in an amplification product;

performing, on each of the samples for which the presence of one or more of the plurality of oligonucleotide tag varieties was confirmed in the first screen, a second screen comprising a series of multiplex polymerase chain reactions, wherein each multiplex polymerase chain reaction comprises a primer set complementary to the first and second unique primer regions of a subset of two or more of the plurality of oligonucleotide tag varieties, and wherein the presence of one or more of the oligonucleotide tag varieties within the subset is confirmed if the multiplex polymerase chain reaction results in an amplification product; and performing, on each subset for which the presence of one or more of the oligonucleotide tag varieties was confirmed in the second screen, an individual polymerase chain reaction for each oligonucleotide tag variety within that subset, wherein each individual polymerase chain reaction comprises a primer set complementary to the first and second unique primer region of one of the plurality of oligonucleotide tag varieties, and wherein the presence of the oligonucleotide tag variety is confirmed if the individual polymerase chain reaction results in an amplification product.

12. The method of claim 11, wherein information about the item of interest is contained within the oligonucleotide tag.

13. The method of claim 11, further comprising the step of sequencing the amplification product of one or more of the polymerase chain reactions.

14. The method of claim 11, wherein each oligonucleotide tag variety is encapsulated by an encapsulant.

* * * * *